United States Patent [19]

Fugitt et al.

[11] 4,128,654
[45] Dec. 5, 1978

[54] 5-HALOMETHYL-3-PHENYL-2-OXAZOLIDINONES

[75] Inventors: Robert B. Fugitt, Newark; Raymond W. Luckenbaugh, Wilmington, both of Del.

[73] Assignee: E. I. Du Pont de Nemours and Company, Wilmington, Del.

[21] Appl. No.: 876,679

[22] Filed: Feb. 10, 1978

[51] Int. Cl.² .................... A61K 31/42; C07D 263/38
[52] U.S. Cl. ............................... 424/272; 260/307 C
[58] Field of Search ..................... 260/307 C; 424/272

[56] References Cited

U.S. PATENT DOCUMENTS 3,641,036  2/1972  Fauran et al. .................. 260/268 C
3,655,687  4/1972  Fauran et al. .................. 260/307 C Primary Examiner—Jose Tovar

[57] ABSTRACT

Compounds of the formula

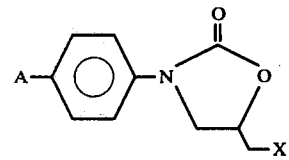

Wherein
A is 1-methylethyl or RS(O)$_n$—;
X is Cl, Br or F;
R is alkyl of 1–3 carbon atoms; and
n is 0, 1 or 2 are effective in controlling fungal and bacterial diseases of plants.

18 Claims, No Drawings

5-HALOMETHYL-3-PHENYL-2-OXAZOLIDINONES

This invention relates to oxazolidinone derivatives which are useful for controlling plant diseases.

Japanese Pat. No. 7,243,809 to Sumitomo Chemical Co., Ltd. discloses and claims an agricultural fungicide which contains the compound (3',5'-dichlorophenyl)-2-oxazolidinone as active ingredient. It is stated that the compound is effective against blast, brown spot and sheath blight which are diseases of rice plants.

Motegi et al., Agrochemicals, 81, 22267 (1974) teaches that oxazolidinone derivatives of the formula

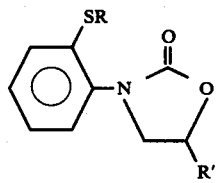

wherein
R is phenyl or benzyl, and
R' is hydrogen or lower alkyl are herbicides.

Neither reference nor any other known reference suggests that systemic control of foliage infections which is obtained with compounds of this invention.

SUMMARY OF THE INVENTION

It has been discovered that the diseases caused by fungi and bacteria which infect living plants, including roots, seeds, tubers, bulbs and other plant parts, can be effectively controlled by applying to the locus of infection the compounds of the formula

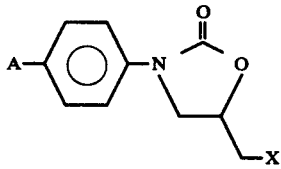

wherein
A is 1-methylethyl or $RS(O)_n$—;
X is Cl, Br or F;
R is alkyl of 1-3 carbon atoms; and
n is 0, 1 or 2.

Preferred on the basis of their biological activity are the compounds of Formula I wherein
A is $RS(O)_n$—;
X is Cl, Br or F;
R is methyl; and
n is 0, 1 or 2.

Most preferred compounds within Formula I on the basis of their favorable cost and highest biological activity are:

5-chloromethyl-3-[4-(1-methylethyl)phenyl]-2-oxazolidinone;
5-chloromethyl-3-[4-methylthiophenyl]-2-oxazolidinone;
5-chloromethyl-3-[4-methylsulfonylphenyl]-2-oxazolidinone; and
5-fluoromethyl-3-[4-methylsulfonylphenyl]-2-oxazolidinone.

A unique characteristic of the compounds of this invention is the systemic control of foliage infections, i.e., when properly applied to a plant part or the surrounding soil according to the method of this invention, the compounds can enter and move about within the plant.

DETAILED DESCRIPTION OF THE INVENTION

The compounds of this invention can be prepared by reacting an appropriately substituted phenyl isocyanate with an epihalohydrin. The isocyanate is added to a solution of the epihalohydrin in a solvent such as dimethylformamide which contains a catalytic amount of lithium halide, such as lithium chloride. The reaction is normally carried out at a temperature in the range of about 75°–120° C., preferably between about 90°–100° C. Temperature is maintained for about 2 to 4 hours, preferably 3 hours. The reaction product can be isolated by slowly adding the reaction solution to a vigorously stirred ice and water mixture. The product will normally separate as a solid and can be recovered by filtration. The reaction product may be purified further, if desired, by recrystallization from an appropriate solvent such as methanol, acetonitrile or chlorobutane.

To prepare those compounds of this invention which contain an oxidized sulfur function, an additional reaction step may be necessary to achieve the desired oxidation state. This may be carried out in an inert solvent, such as methylene chloride, using an oxidizing agent such as metachloroperoxybenzoic acid. The methods used to isolate the reaction product are well known to those skilled in the art, and will depend upon the particular oxidizing agent chosen.

The following examples further describe how compounds of this invention may be prepared.

EXAMPLE 1

Preparation of 5-chloromethyl-3-[4-(1-methylethyl)phenyl]-2-oxazolidinone 0.2–0.3 grams of lithium chloride was added to a solution of 7 grams (0.076 mole) epichlorohydrin in 30 ml dimethylformamide at 90° C. Heating was discontinued, and a solution of 12.25 grams (0.076 mole) 4(1-methylethyl)phenylisocyanate in 10 ml dimethylformamide was added dropwise at such a rate that the reaction temperature did not exceed 110° C. When the addition was complete heat was reapplied and the reaction solution was stirred at 90° C. for 3 hours. The solution was then added in a slow stream to a vigorously stirred mixture of ice and water, about 200 ml total volume. The reaction product solidified and was recovered by filtration. Recrystallization from methanol afforded an 85% yield of white crystalline material (mp 77°–79° C.).

EXAMPLE 2

Preparation of 5-Bromomethyl-3-(4-methylthio)phenyl-2-oxazolidinone.

0.1–0.2 grams of lithium bromide was added to a solution of 4.15 grams (0.03 mole) epibromohydrin in 20 ml dimethylformamide at 90° C. Heating was discontinued and a solution of 5 grams (0.03 mole) 4-methylthiophenylisocyanate in 5 ml dimethylformamide was added at such a rate that the reaction temperature did not exceed 110° C. When the addition was complete, heat was reapplied, and the reaction solution was stirred at 90° C. for 3 hours. The reaction solution was then poured slowly with stirring into a 200 ml mixture of ice and water. The product was isolated by filtration and recrystallized from methanol to give an 80% yield of white crystalline material (mp 101°-104° C.).

EXAMPLE 3

Preparation of 5-fluoromethyl-3-(4-methylsulfonyl)-phenyl-2-oxazolidinone.

Five grams (0.019 mole) 5-fluoromethyl-3-(4-methylthio)phenyl-2-oxazolidinone (prepared as described in Examples 1 and 2) was added to 150 ml methylene chloride. The resulting suspension was heated to reflux, and a solution of 8.2 grams (0.047 mole) meta-chloroperoxybenzoic acid in 150 ml methylene chloride was slowly added. Reflux was continued for 2 hours. The methylene chloride solution was filtered and washed three times with saturated sodium bicarbonate solution. The methylene chloride layer was dried over magnesium sulfate and then evaporated. The residue was recrystallized from a mixture of methanol and acetonitrile affording a 70% yield of white crystalline material (mp 175°-177° C.). By following the methods of Examples 1 and 2 and, where applicable, the method described in Example 3, the compounds listed in Table 1 can be prepared.

TABLE 1

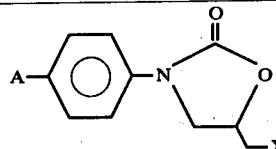

| A | X | mp (C°) |
|---|---|---|
| 1-methylethyl | Br | 83–86 |
| 1-methylethyl | F | 91–92 |
| methylthio | Cl | 96–99 |
| methylthio | F | 99–102 |
| methylsulfinyl | Cl | — |
| methylsulfonyl | Br | 165–168 |
| methylsulfonyl | Cl | 171–173 |
| ethylthio | Br | — |
| 1-methylethylsulfonyl | Cl | 140–143 |
| n-propylsulfinyl | Br | — |
| 1-methylethylthio | Cl | 95–99 |
| 1-methylethylthio | Br | — |
| 1-ethylsulfonyl | Cl | — |
| 1-ethylsulfonyl | Br | — |
| 1-ethylsulfonyl | F | — |
| 1-methylethylsulfonyl | Br | — |

The compounds of this invention are effective in controlling plant diseases caused by fungal pathogens represented by Phytophthora infestans, Plasmopora viticola and Pythium spp, and by bacterial pathogens represented by Agrobacterium tumefaciens and Xanthomonas vesicatoria. Disease control is accomplished by applying the compound of this invention to the portion of the plant to be protected or to the roots, stems, seeds, tubers or bulbs of the plant or to the soil in which the plant is growing for a systemic effect in untreated plant parts. The compound may be applied as a preventive treatment prior to inoculation by the pathogen, or after inoculation as a curative, post-infection treatment.

Rates of application for these compounds will be influenced by many factors of the environment and must be determined under use conditions. Foliage sprayed with a concentration of from 50 to about 500 ppm active ingredient can be protected from disease under some conditions. Seed and seedlings can normally be protected when seed is treated at a rate of from 0.3 to about 3 grams per kilogram of seed. Plants growing in soil treated at a concentration of from 2 to about 20 kg/ha can be protected from disease because compounds of this invention can enter the plants through the roots and can move throughout the plant. Compositions of this invention may contain, in addition to the compounds of this invention, conventional pesticides, such as insecticides, miticides, bactericides, nematicides, fungicides or other agricultural chemicals such as growth modifying agents and fertilizer ingredients, and the like. The proper choice of conventional pesticide and their amounts can be made by one skilled in the art of protecting plants from pest depredation. In the following examples, which more clearly illustrate the biological activity of the compounds of this invention, percent disease control was calculated by the formula $$100 - \left[ \frac{\text{disease rating on treated}}{\text{disease rating on untreated}} \times 100 \right] = \text{percent control}$$

EXAMPLE 4

5 week old Bonnie Best tomato plants, growing in 10 cm plastic pots of soil were used as hosts for tomato late blight in the greenhouse.

Compounds of this invention were dissolved in acetone in an amount equal to 10% of the final volume and then suspended at a concentration of 80 ppm in purified water containing 250 ppm of the surfactant, TREM ® 014 (polyhydric alcohol esters). This suspension was sprayed to the point of run-off on the tomato plants. The next day the plants were inoculated with a spore suspension of the fungus, Phythophthora infestans, incubated in a saturated humidity at 20° C. for 25 hours and then further incubated in the greenhouse an additional three days. Disease ratings were made for each treatment. Test results are shown in Table 2.

TABLE 2

| Compound | Tomato Late Blight Percent Control |
|---|---|
| 5-(chloromethyl)-3-(4-methylthio-phenyl)-2-oxazolidinone | 95 |
| 5-(chloromethyl)-3-(4-methylsulfonyl phenyl)-2-oxazolidinone | 100* |
| 5-(bromomethyl)-3-[4-(1-methylethyl) phenyl]-2-oxazolidinone | 98 |
| 5-(fluoromethyl)-3-[4-(methylthio) phenyl]-2-oxazolidinone | 85 |
| 5-(fluoromethyl)-3-[4-(1-methylethyl) phenyl]-2-oxazolidinone | 100 |
| 5-(bromoethyl)-3-[4-(methylsulfonyl) phenyl]-2-oxazolidinone | 100* |
| 5-(chloromethyl)-3-[4-(1-methylpropyl) phenyl]-2-oxazolidinone | 45 |
| 5-fluoromethyl-3-(4-methylsulfonylphenyl)-2-oxazolidinone | 98* |

*Some chlorosis was observed on the youngest foliage.

EXAMPLE 5

The curative, post-infection control achieved with compounds of this invention was demonstrated on 5 week old Bonnie Best tomato plants. These were growing in 10 cm plastic pots of soil and were used as hosts for tomato late blight in the greenhouse. The plants were inoculated with a spore suspension of the fungus, Phytophothora infestans, incubated in a saturated humidity at 20° C. for 6 hours, and then air-dried.

Compounds of this invention were dissolved in acetone in an amount equal to 10% of the final volume, and then suspended at a concentration of 80 ppm in purified water containing 250 ppm of the surfactant, TREM ® 014 (polyhydric alcohol esters). This suspension was sprayed to the point of run-off on the plants that had been inoculated. The chemically-sprayed and inoculated plants were incubated again in a saturated humidity at 20° C. overnight, and then in the greenhouse an additional three days. Disease ratings were made for each treatment. Test results may be seen in Table 3.

TABLE 3

| Compound | Tomato Late Blight Percent Control |
|---|---|
| 5-(chloromethyl)-3-(4-methylthio-phenyl)-2-oxazolidinone | 89 |
| 5-(chloromethyl)-3-(4-methylsulfonyl phenyl)-2-oxazolidinone | 95* |
| 5-(bromomethyl)-3-[4-(1-methylethyl) phenyl]-2-oxazolidinone | 89 |

*Some chlorosis was observed on the youngest foliage.

EXAMPLE 6

The systemic effects of the compounds of this invention were demonstrated on 5 week old Bonnie Best tomato plants, growing in 10 cm plastic pots of soil which were used as hosts for tomato late blight in the greenhouse.

Compounds of this invention were dissolved in acetone in an amount equal to 10% of the final volume, and then suspended at a concentration of 160 ppm in purified water containing 250 ppm of the surfactant, TREM ® 014 (polyhydric alcohol esters). Twenty-five ml of the suspension containing 4 mg of the chemical was drenched on the soil of each 10 cm pot. This is 5 kg/ha on a weight/weight basis. Twenty-four hours later, the chemically-drenched tomato plants were inoculated with a spore suspension of the fungus, Phytophthora infestans, incubated in a saturated humidity at 20° C. for 24 hours, and then further incubated in the greenhouse an additional 3 days. Disease ratings were made for each treatment, and the results may be seen in Table 4.

TABLE 4

| Compound | Tomato Late Blight Percent Control |
|---|---|
| 5-(chloromethyl)-3-(4-methylthio phenyl)-2-oxazolidinone | 99 |
| 5-(chloromethyl)-3-(4-methylsulfonyl phenyl)-2-oxazolidinone | 100 |
| 5-(bromomethyl)-3-[4-(1-methylethyl) phenyl]-2-oxazolidinone | 83 |
| 5-(fluoromethyl)-3-(4-methylthio-phenyl)-2-oxazolidinone | 100* |
| 5-(fluoromethyl)-3-[4-(1-methylethyl) phenyl]-2-oxazolidinone | 100 |

*Some chlorosis was observed on the youngest foliage.

EXAMPLE 7

The control of grape downy mildew (Plasmopora viticola) was demonstrated in preventive and curative, post-infection tests on the leaves of Vitis labrusca cultivar Delaware grown in the greenhouse. Compounds of this invention were dissolved in acetone in an amount equal to 10% of the final volume and suspended in purified water with 250 ppm of the surfactant TREM ® 014 (polyhydric alcohol esters). For preventive tests, compounds were applied to the point of run-off at a concentration of 80 ppm one day prior to inoculation. In curative tests, the compounds were applied at a concentration of 100 ppm 24 hours after inoculation with the pathogen. Inoculation was made by spraying the leaves with a sporangial suspension and incubating in a saturated humidity chamber for 12 days. Disease ratings were made for each treatment Test results may be seen in Table 5.

TABLE 5

| | % Disease Control | |
|---|---|---|
| Compounds Tested | Preventive | Curative |
| 5-(chloromethyl)-3-(4-methylthio-phenyl)-2-oxazolidinone | 100 | 100 |
| 5-(chloromethyl)-3-(4-methylsulfonyl-phenyl)-2-oxazolidinone | 100 | 100 |
| 5-(fluoromethyl)-3-(4-methylsulfonyl-phenyl)-2-oxazolidinone | 100 | 100 |
| 5-(fluoromethyl)-3-[4-(1-methylethyl) phenyl]-2-oxazolidinone | 100 | 88 |
| 5-fluoromethyl-3-(4-methylthiophenyl)-2-oxazolidinone | 100 | 100 |

EXAMPLE 8

The control of seed and seedling rot from Pythium spp. was demonstrated on cotton planted in soil in the greenhouse. Cotton (acid delinted) seed was treated with a surface application of 5-(chloromethyl)-3-(4-methylsulfonyl phenyl)-2-oxazolidinone at a rate of 0.6 grams per kilogram of seed. The compound, dissolved in acetone, was transferred from the surface of a glass jar to untreated cotton seed by tumbling the seed in the jar for 5 minutes. Untreated seed planted in soil containing pathogenic Pythium spp. failed to emerge while 88 percent of the treated seed emerged and produced healthy seedlings during the same test period.

EXAMPLE 9

The control of bacterial diseases of plants with the compounds of this invention was demonstrated on Bonnie Best tomato plants grown in the greenhouse. Compounds were dissolved in acetone and suspended at a concentration of 200 ppm in water containing 450 ppm of of the surfactant TREM ® 014 (polyhydric alcohol esters). This suspension was sprayed to the point of run-off on the plants. The next day the stems of some of the plants were inoculated with Agrobacterium tumefaciens and the foliage of some of the plants was inoculated with Xanthomonos vesticatoria. After a suitable incubation period, after the untreated plants were heavily diseased with crown galls or bacterial leaf spots, disease ratings were made. Treated plants had some chlorosis on the youngest foliage. Results for two of the compounds of this invention may be seen in Table 6.

TABLE 6

| | Percent Control | |
|---|---|---|
| Compound | Crown Gall | Leaf Spot |
| 5-(chloromethyl)-3-(4-methylthio-phenyl)-2-oxazolidinone | 100 | 65 |
| 5-(chloromethyl)-3-(4-methylsul-fonyl phenyl)-2-oxazolidinone | 100 | 65 |

Useful formulations of the compounds of this invention can be prepared as dusts, granules, pellets, solutions, suspensions, emulsions, wettable powders, emulsifiable concentrates and the like. Many of these may be applied directly. However, sprayable formulations are normally extended in suitable media and used at spray volumes of from a few pints to several hundred gallons per acre. High strength compositions are primarily used as intermediates for further formulation. The formulations, broadly, contain from about 1% to 99% by weight of active ingredient and at least one of a) about 0.1% to 20% by weight surfactant(s) and b) about 5% to 99% by weight solid or liquid diluent(s). More specifically, they will contain these ingredients in the following approximate proprotions.

|  | Percent by Weight | | |
| --- | --- | --- | --- |
|  | Active Ingredient | Diluent(s) | Surfactant(s) |
| Wettable Powders | 20-90 | 0-74 | 1-10 |
| Oil Suspensions, Emulsions, Solutions (including Emulsifiable Concentrates) | 5-50 | 40-95 | 0-15 |
| Aqueous Suspensions | 10-50 | 40-84 | 1-20 |
| Dusts | 1-25 | 70-99 | 0-5 |
| Granules and Pellets | 1-95 | 5-99 | 0-15 |
| High Strength Compositions | 90-99 | 0-10 | 0-2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd. Edn., Dorland Books, Caldwell, N.J. The more absorptive diluents are preferred for wettable powders and the denser ones for dusts. Typical liquid diluents and solvents are described in Marsden, "Solvents Guide", 2nd. Edn., Interscience, New York, 1950. Solubility under 0.1% is preferred for suspension concentrates; solution concentrates are preferably stable against phase separation at 0° C. "McCutcheon's Detergents and Emulsifiers Annual", Allured Publ. Corp., Ridgewood, New Jersey, as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc.

The methods of making the compositions of this invention are known in the art. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon performed granular carriers or by any convenient agglomeration technique. The following examples further illustrate the compositions of this invention.

EXAMPLE 10

| Wettable Powder | |
| --- | --- |
| 5-chloromethyl-3-(4-methylsulfonylphenyl)-2-oxazolidinone | 50% |
| sodium alkylnaphthalenesulfonate | 2% |
| low viscosity methyl cellulose | 2% |
| diatomaceous earth | 46% |

The ingredients are blended, coarsely hammer milled and then air milled to produce particles of active essentially all below 10 microns in diameter. The product is reblended before packaging.

EXAMPLE 11

| Wettable Powder | |
| --- | --- |
| 5-chloromethyl-3-[4-(1-methylethyl) phenyl]-2-oxazolidinone | 40% |
| dioctyl sodium sulfosuccinate | 1.5% |
| sodium ligninsulfonate | 3% |
| low viscosity methyl cellulose | 1.5% |
| attapulgite | 54% |

The ingredients are thoroughly blended, passed through an air mill, to produce an average particle size under 15 microns, reblended, and sifted through a U.S.S. No. 50 sieve (0.3 mm opening) before packaging.

All compounds of the invention may be formulated in the same manner.

EXAMPLE 12

| Granule | |
| --- | --- |
| wettable powder of Example 1 | 15% |
| gypsum | 69% |
| potassium sulfate | 16% |

The ingredients are blended in a rotating mixer and water sprayed on to accomplish granulation. When most of the material has reached the desired range of 1.0 to 0.42 mm. (U.S.S. # 18 to 40 sieves), the granules are removed, dried, and screened. Oversize material is crushed to produce additional material in the desired range. These granules contain 7.5% by weight active ingredient.

EXAMPLE 13

| Oil Suspension | |
| --- | --- |
| 5-chloromethyl-3-(4-methylthiophenyl)-2-oxazolidinone | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

What is claimed is:

1. A compound of the formula

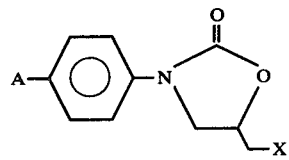

wherein
A is 1-methylethyl or RS(O)$_n$—;
X is Cl, Br or F;
R is alkyl of 1-3 carbon atoms; and
n is 0, 1 or 2.

2. The compound of claim 1 wherein
A is RS(O)$_n$—;
R is methyl;
X is Cl, F or Br; and
n is 0, 1 or 2.

3. The compound of claim 1 which is 5-chloromethyl-3-[4-(1-methylethyl)phenyl]-2-oxazolidinone.

4. The compound of claim 1 which is 5-chloromethyl-3-[4-methylthiophenyl]-2-oxazolidinone.

5. The compound of claim 1 which is 5-chloromethyl-3-[4-methylsulfonylphenyl]-2-oxazolidinone.

6. The compound of claim 1 which is 5-fluoromethyl-3-[4-methylsulfonylphenyl]-2-oxazolidinone.

7. A disease control composition consisting essentially of an effective amount of a compound of claim 1 and at least one of a) about 0.01% to 20% by weight surfactant(s) and b) about 5 to 99% by weight solid or liquid diluent(s).

8. A disease control composition consisting essentially of an effective amount of a compound of claim 2 and at least one of a) about 0.1% to 20% by weight surfactant(s) and b) about 5 to 99% by weight solid or liquid diluent(s).

9. A disease control composition consisting essentially of an effective amount of a compound of claim 3 and at least one of a) about 0.1% to 20% by weight surfactant(s) and b) about 5 to 99% by weight solid or liquid diluent(s).

10. A disease control composition consisting essentially of an effective amount of a compound of claim 4 and at least one of a) about 0.1% to 20% by weight surfactant(s) and b) about 5 to 99% by weight solid or liquid diluent(s).

11. A disease control composition consisting essentially of an effective amount of a compound of claim 5 and at least one of a) about 0.1% to 20% by weight surfactant(s) and b) about 5 to 99% by weight solid or liquid diluent(s).

12. A disease control composition consisting essentially of an effective amount of a compound of claim 6 and at least one of a) about 0.1% to 20% by weight surfactant(s) and b) about 5 to 99% by weight solid or liquid diluent(s).

13. A method for controlling diseases of plants which comprises applying to the locus to be protected an effective amount of a compound of claim 1.

14. A method for controlling diseases of plants which comprises applying to the locus to be protected an effective amount of a compound of claim 2.

15. A method for controlling diseases of plants which comprises applying to the locus to be protected an effective amount of a compound of claim 3.

16. A method for controlling diseases of plants which comprises applying to the locus to be protected an effective amount of a compound of claim 4.

17. A method for controlling diseases of plants which comprises applying to the locus to be protected an effective amount of a compound of claim 5.

18. A method for controlling diseases of plants which comprises applying to the locus to be protected an effective amount of a compound of claim 6.

* * * * *